(12) United States Patent
Schoeny

(10) Patent No.: US 11,262,344 B2
(45) Date of Patent: Mar. 1, 2022

(54) SYSTEM AND METHOD FOR MANAGING MATERIAL ACCUMULATION RELATIVE TO A GROUND ENGAGING ASSEMBLY OF AN AGRICULTURAL IMPLEMENT BASED ON THE ACCUMULATION TYPE

(71) Applicant: CNH Industrial America LLC, New Holland, PA (US)

(72) Inventor: Christopher Schoeny, Yorkville, IL (US)

(73) Assignee: CNH Industrial America LLC, New Holland, PA (US)

( * ) Notice: Subject to any disclaimer, the term of this patent is extended or adjusted under 35 U.S.C. 154(b) by 305 days.

(21) Appl. No.: 16/408,740

(22) Filed: May 10, 2019

(65) Prior Publication Data
US 2020/0355667 A1 Nov. 12, 2020

(51) Int. Cl.
*G01N 33/24* (2006.01)
*A01B 63/16* (2006.01)
(Continued)

(52) U.S. Cl.
CPC ........... *G01N 33/246* (2013.01); *A01B 63/16* (2013.01); *A01B 63/22* (2013.01); *A01B 79/005* (2013.01); *A01B 27/005* (2013.01); *A01C 5/064* (2013.01); *A01C 5/068* (2013.01); *A01C 7/08* (2013.01); *G01N 2033/245* (2013.01)

(58) Field of Classification Search
CPC ........... G01N 33/246; G01N 2033/245; G01N 33/24; G01N 33/00; A01B 63/16; A01B 79/005; A01B 63/14; A01B 63/00; A01B 79/00; A01B 27/00; A01B 63/22; A01B 27/005; A01C 5/064; A01C 5/068;
(Continued)

(56) References Cited

U.S. PATENT DOCUMENTS 4,286,424 A 9/1981 Hubbard
6,843,044 B2 1/2005 Clauss
(Continued)

FOREIGN PATENT DOCUMENTS

AU 2017101791 A4 2/2018
EP 2377385 B1 10/2011

OTHER PUBLICATIONS

Case IH 2017 Productivity Guide, accessed Feb. 11, 2019, https://www.centralilag.com/fckimages/literature-showroom/2000-Planter-Productivity-Guide.pdf, 56 pages.

*Primary Examiner* — Christopher J. Novosad
(74) *Attorney, Agent, or Firm* — Rebecca L. Henkel; Rickard K. DeMille

(57) ABSTRACT

In one aspect, the present subject matter is directed to a system for managing material accumulation relative to a ground engaging assembly of an agricultural implement. The system may include one or more ground engaging tools of the ground engaging assembly, a sensor detecting material accumulation relative to the ground engaging tools, and a controller communicatively coupled to the sensor. The controller may receive an input from the sensor associated with material accumulation relative to the ground engaging tools. The controller may further access data associated with an amount of crop residue present and data associated with a moisture content of soil within the field. Additionally, the controller may determine an accumulation type of the material accumulation based at least in part on the crop residue data and the soil moisture data.

20 Claims, 5 Drawing Sheets

(51) Int. Cl.
*A01B 63/22* (2006.01)
*A01B 79/00* (2006.01)
*A01C 5/06* (2006.01)
*A01C 7/08* (2006.01)
*A01B 27/00* (2006.01)

(58) Field of Classification Search
CPC .......... A01C 7/08; A01C 5/062; A01C 5/066; A01C 7/00
See application file for complete search history.

(56) References Cited

U.S. PATENT DOCUMENTS

| | | |
|---|---|---|
| 7,381,130 B2 | 6/2008 | Smith |
| 8,408,149 B2 | 4/2013 | Rylander |
| 8,833,680 B2 | 9/2014 | Ellingson et al. |
| 8,849,523 B1 | 9/2014 | Chan et al. |
| 9,282,688 B2 | 3/2016 | Casper et al. |
| 9,405,039 B2 | 8/2016 | Anderson |
| 9,485,900 B2 | 11/2016 | Connell et al. |
| 9,928,606 B2 | 3/2018 | Roth et al. |
| 9,943,027 B2 | 4/2018 | Sauder et al. |
| 10,091,932 B2 | 10/2018 | Neitemeier et al. |
| 2017/0112043 A1 | 4/2017 | Nair et al. |

SYSTEM AND METHOD FOR MANAGING MATERIAL ACCUMULATION RELATIVE TO A GROUND ENGAGING ASSEMBLY OF AN AGRICULTURAL IMPLEMENT BASED ON THE ACCUMULATION TYPE

FIELD OF THE INVENTION

The present disclosure generally relates to agricultural implements, and more particularly, to a system and an associated method for managing material accumulation relative to a ground engaging assembly of an agricultural implement based on a determination of the accumulation type of the material accumulation.

BACKGROUND OF THE INVENTION

Modern farming practices strive to increase yields of agricultural fields. In this respect, certain agricultural implements, such as seed-planting implements, are towed behind a tractor or other work vehicle for planting. A seed-planting implement typically includes one or more ground engaging assemblies configured to work the soil as the implement is moved across a field. For example, in certain configurations, the implement may include one or more opening assemblies that form a trench or furrow within the soil as the implement is moved across the field. Furthermore, the implement may also include one or more closing assemblies that close the furrow while the implement is moved across the field. In this regard, the function(s) of the ground engaging tool(s) requires or relies upon movement of the field materials, such as soil and/or crop residue, relative to the assemblies.

Typically, the ground engaging assemblies are configured to work the soil in a specific way. For example, each closing assembly may include a pair of closing tools, with the closing tools being configured to work together to sufficiently close a furrow over a seed placed in the furrow. As agricultural operations are performed, excessive amounts of field material may build up or accumulate relative to the closing assemblies, for example, in front of, between, or behind the closing tools of the closing assemblies. Such material accumulation can limit or prevent the closing tools from properly closing the furrow, which negatively affects yields. Depending on the accumulation type of the material built up relative to the closing assemblies, certain methods may be unsuccessful in managing the material accumulation and the performance of such unsuccessful methods can negatively impact the operating efficiency of the closing assembly and/or the overall efficiency of the agricultural operation being performed.

Accordingly, an improved system and method for managing material accumulation based on the type of material accumulating relative to a ground engaging assembly of an agricultural implement would be welcomed in the technology.

BRIEF DESCRIPTION OF THE INVENTION

Aspects and advantages of the invention will be set forth in part in the following description, or may be obvious from the description, or may be learned through practice of the invention.

In one embodiment, the present subject matter is directed to a system for managing material accumulation during operation of an agricultural implement. The system includes a ground engaging assembly including one or more ground engaging tools configured to engage soil within a field as the agricultural implement is moved across the field, a sensor detecting material accumulation relative to the one or more ground engaging tools, and a controller communicatively coupled to the sensor. The controller has a processor and an associated memory, the memory including instructions that, when implemented by the processor, configure the controller to receive an input from the sensor associated with material accumulation relative to the one or more ground engaging tools. The instructions further configure the controller to access crop residue data associated with an amount of crop residue present within the field and access soil moisture data associated with a moisture content of soil within the field. Additionally, the instructions configure the controller to determine an accumulation type of the material accumulation based at least in part on the crop residue data and the soil moisture data.

In another embodiment, the present subject matter is directed to a method for managing material accumulation relative to a ground engaging assembly of an agricultural implement, where the ground engaging assembly includes one or more ground engaging tools configured to engage soil within a field as the agricultural implement is moved across the field. The method includes receiving, at or with a computing device, an input associated with material accumulation relative to the one or more ground engaging tools. The method further includes accessing, with the computing device, crop residue data associated with an amount of crop residue present within the field. Further, the method includes accessing, with the computing device, soil moisture data associated with a moisture content of soil within the field. Moreover, the method includes determining, with the computing device, an accumulation type of the material accumulation based at least in part on the crop residue data and the soil moisture data. Additionally, the method includes performing, with the computing device, a control action based on the determination of the accumulation type of the material accumulation relative to the one or more ground engaging tools.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
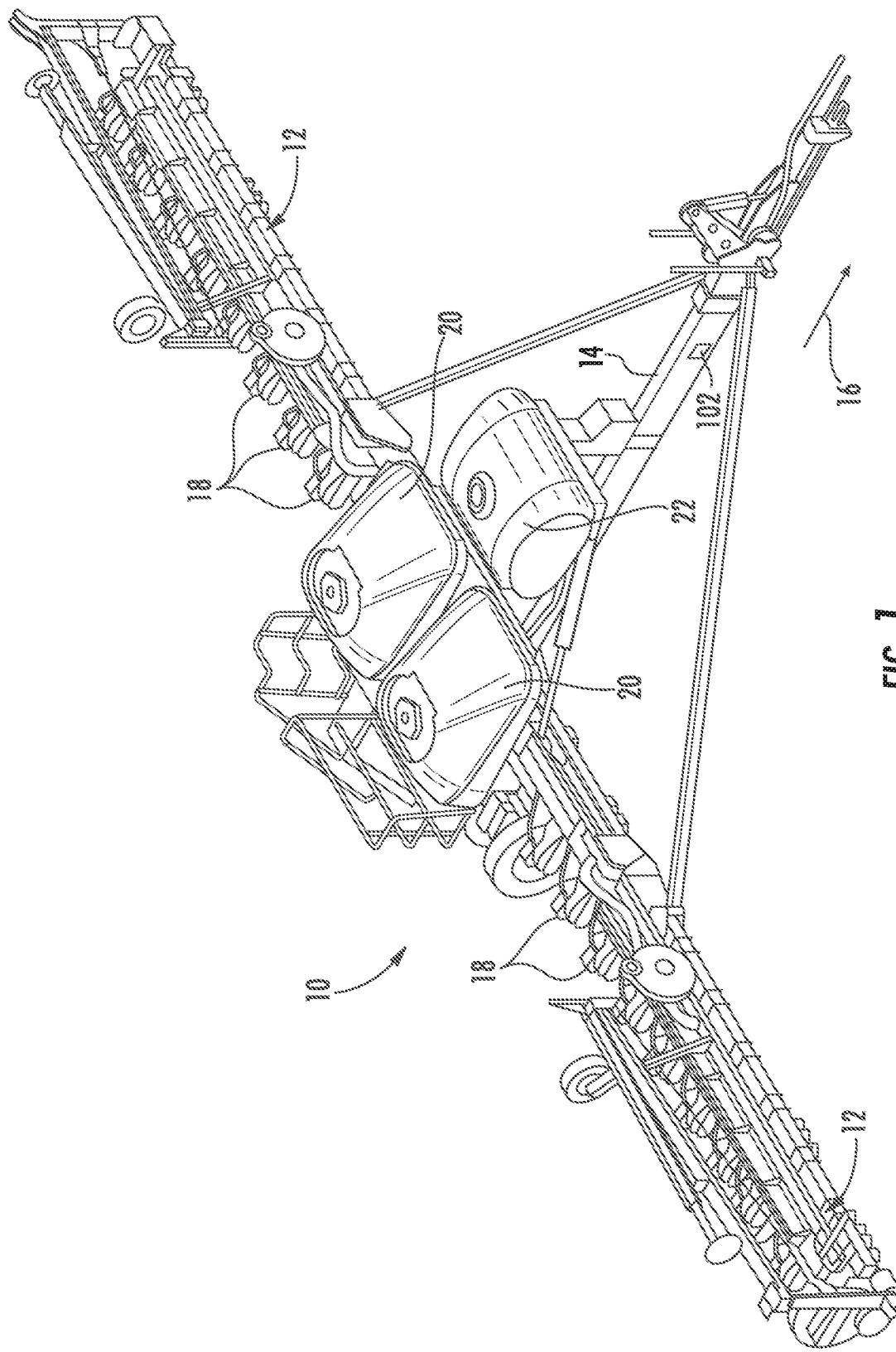
FIG. 1 illustrates a perspective view of one embodiment of a seed-planting implement in accordance with aspects of the present subject matter.

Repeat use of reference characters in the present specification and drawings is intended to represent the same or analogous features or elements of the present technology.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as conic within the scope of the appended claims and their equivalents.

In general the present subject matter is directed to systems and methods for managing material accumulation relative to a ground engaging assembly of an agricultural implement, such as a closing assembly of the implement. Specifically, in several embodiments, as the implement is being moved across a field, one or more ground engaging tool(s) are configured to engage the soil of the field. Depending on the field or operating conditions, the ground engaging tool(s) may experience "plugging," or excessive material accumulation of soil, residue, and/or other field materials to the point where the tool(s) cannot properly and/or efficiently work the soil.

In accordance with aspects of the present subject matter, when material accumulation or plugging is detected relative to one or more of the ground engaging tools of an agricultural implement, a controller of the disclosed system may be configured to access crop residue data and soil moisture data respectively associated with an amount of crop residue and a soil moisture present within the field (e.g., at or adjacent to the current location of the agricultural implement, including field locations previously passed over by the implement during operation with the field). Based on the accessed data, the controller may be configured to determine the type of the material accumulating relative to the tools) (i.e., an "accumulation type"). For instance, the controller may determine that the accumulation type corresponds to one of residue-based plugging, mud-based plugging, and/or rock-based plugging based on the available residue/moisture data. Thereafter, the controller may be configured to automatically perform a control action suitable for the determined accumulation type.

Referring now to the drawings, FIG. 1 illustrates a perspective view of one embodiment of an agricultural implement 10 in accordance with aspects of the present subject matter. It should be appreciated that, although the agricultural implement 10 illustrated herein corresponds to a seed-planting implement or planter, the implement 10 may generally correspond to any suitable equipment or implement having tools configured to engage the soil within a field, such as a tillage implement, and/or the like.

As shown in FIG. 1, the implement 10 may include a laterally extending toolbar or frame assembly 12 connected at its middle to a forwardly extending tow bar 14 to allow the implement 10 to be towed by a work vehicle (not shown), such as an agricultural tractor, in a direction of travel (e.g., as indicated by arrow 16 in FIG. 1). The toolbar 12 may generally be configured to support a plurality of seed planting units (or row units) 18. As is generally understood, each row unit 18 may be configured to deposit seeds at a desired depth beneath the soil surface and at a desired seed spacing as the implement 10 is being towed by the work vehicle, thereby establishing rows of planted seeds. In some embodiments, the bulk of the seeds to be planted may be stored in one or more hoppers or seed tanks 20. Thus, as seeds are planted by the row units 18, a pneumatic distribution system may distribute additional seeds from the seed tanks 20 to the individual row units 18. Additionally, one or more fluid tanks 22 may store agricultural fluids, such as insecticides, herbicides, fungicides, fertilizers, and/or the like.

It should be appreciated that, in general, the implement 10 may include any number of row units 18, such as six, eight, twelve, sixteen, twenty-four, thirty-two, or thirty-six row units. In addition, it should be appreciated that the lateral spacing between row units 18 may be selected based on the type of crop being planted. For example, the row units 18 may be spaced approximately thirty inches from one another for planting corn, and approximately fifteen inches from one another for planting soybeans.

Additionally, as shown in FIG. 1, in several embodiments, one or more soil moisture sensors 102 may be provided operative association with the implement 10, such as by mounting the sensor(s) 102 on a portion(s) of the frame assembly 12 and/or tow bar 14 and/or by mounting the sensor(s) one or more of the row units 18. The soil moisture sensor(s) 102 may generally be configured to detect a parameter associated with the moisture content of the soil within the field across which the implement 10 is being moved. For example, in one embodiment, the soil moisture sensor(s) 102 may be configured as an optical sensor(s) configured to detect one or more characteristics of light reflected by the soil, with such characteristics generally being indicative of the soil moisture content. However, it should be appreciated that, in alternative embodiments, the soil moisture sensor(s) 102 may be configured as any other suitable device for sensing or detecting the moisture content of the soil, such as a contact resistance sensor or any other contact-based sensing device configured to engage or contact the soil as the implement 10 is towed across the field.

It should also be appreciated that the configuration of the seed-planting implement 10 described above and shown in FIG. 1 is provided only to place the present subject matter in an exemplary field of use. Thus, it should be appreciated that the present subject matter may be readily adaptable to any manner of implement configuration. For example, the implement 10 may instead be configured as a tillage implement having one or more ground engaging assemblies capable of experiencing material accumulation, such as one or more tillage assemblies having disc harrows or rolling baskets.

Figure 2:
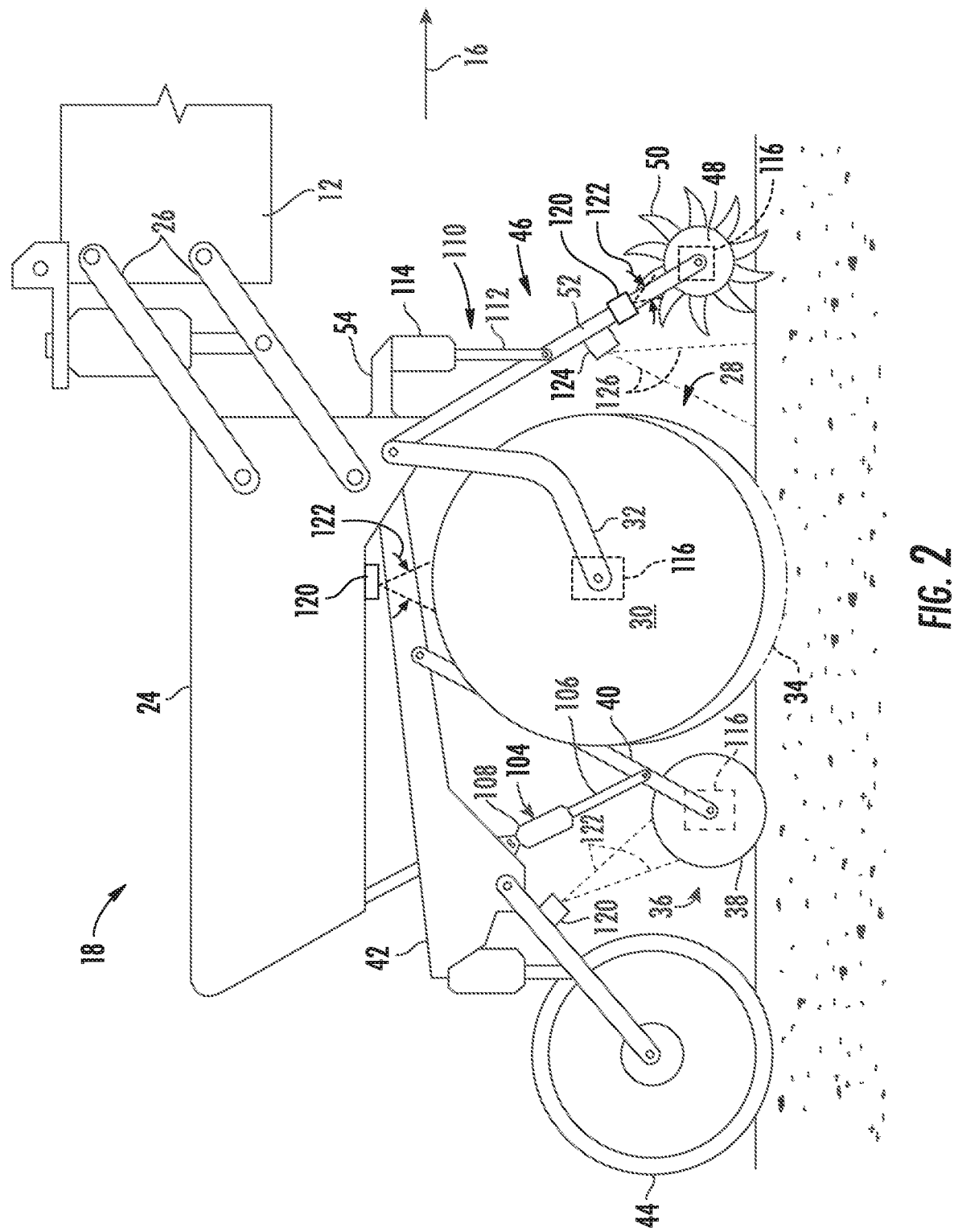
FIG. 2 illustrates a side view of one embodiment of a row unit suitable for use with a seed-planting implement in accordance with aspects of the present subject matter.

Referring now to FIG. 2, a side view of one embodiment of a row unit 18 is illustrated in accordance with aspects of the present subject matter. As shown, the row unit 18 may include a frame 24 adjustably coupled to the toolbar 12 by links 26. For example, one end of each link 26 may be pivotably coupled to the frame 24, while an opposed end of each link 26 may be pivotably coupled to the toolbar 12. In one embodiment, the links 26 may be parallel. However, it should be appreciated that, in alternative embodiments, the row unit 18 may be coupled to the toolbar 12 in any other suitable manner.

As shown in FIG. 2, the row unit 18 also includes a furrow opening assembly 28. For example, in one embodiment, the furrow opening assembly 28 may include a gauge wheel 30 operatively coupled to the frame 24 of the row unit 18 via a support arm 32. Furthermore, the opening assembly 28 may also include disc openers 34 (only one of which is shown configured to excavate a furrow or trench in the soil. As is generally understood, the gauge wheel 30 may be configured to engage the top surface of the soil as the implement 10 is moved across the field. In this regard, the height of the disc opener(s) 34 may be adjusted with respect to the position of the gauge wheel 30 to set the desired depth of the furrow being excavated.

Moreover, as shown, the row unit 18 may include a furrow closing assembly 36. Specifically, in several embodiments, the furrow closing assembly 36 may include a pair of closing discs 38 (only one of which is shown) positioned relative to each other in a manner that permits soil to flow between the discs 38 as the implement 10 is being moved across the field. As such, the closing discs 38 may be configured to close the furrow after seeds have been deposited therein, such as by pushing the excavated soil into the furrow. Furthermore, the furrow closing assembly 36 may include a support arm 40 configured to adjustably couple the closing discs 38 to the frame assembly 24. For example, one end of the support arm 40 may be pivotally coupled to the closing discs 38, while an opposed end of the support arm 40 may be pivotally coupled to a chassis arm 42, which is, in turn, coupled to the frame 24. However, it should be appreciated that, in alternative embodiments, the closing discs 38 may be coupled to the frame 24 in any other suitable manner. Furthermore, it should be appreciated that, in alternative embodiments, the furrow closing assembly 36 may include any other suitable number of closing discs 38, such as one closing disc 38 or three or more closing discs 38. Additionally, the furrow closing assembly 36 may include a press wheel 44 configured to roll over the closed furrow to firm the soil over the seed and promote favorable seed-to-soil contact.

In one embodiment, an actuator 104 may be configured to move or otherwise adjust the position of the furrow closing assembly 36 relative to the frame 24. For example, as shown in the illustrated embodiment, a first end of the actuator 104 (e.g., a rod 106 of the actuator 104) may be coupled to the support arm 40 of the furrow closing assembly 36, while a second end of the actuator 104 (e.g., the cylinder 108 of the actuator 104) may be coupled to the chassis arm 42, which is, in turn, coupled to the frame 24. The rod 106 of the actuator 104 may be configured to extend and/or retract relative to the cylinder 108 to adjust the downforce being applied to and/or the penetration depth of the closing disc(s) 38. In addition, such extension and/or retraction may move the furrow closing assembly 36 between an operating position relative to the ground in which the closing disc(s) 38 engages the soil and a raised position relative to the ground in which the closing disc(s) 38 is lifted out of the soil. In the illustrated embodiment, the actuator 104 corresponds to a fluid-driven actuator, such as hydraulic or pneumatic cylinder. However, it should be appreciated that the actuator 104 may correspond to any other suitable type of actuator, such as an electric linear actuator.

Additionally, as shown in FIG. 2, the row unit 18 may include a residue removal device 46 positioned at the forward end of the row unit 18 relative to the direction of travel 16. In this regard, the residue removal device 46 may be configured to break up and/or sweep away residue, dirt clods, and/or the like from the path of the row unit 18 before the furrow is formed in the soil. For example, in one embodiment, the residue removal device 46 may include one or more residue removal wheels 48, with each wheel 48 having a plurality of tillage points or fingers 50. As such, the wheel(s) 48 may be configured to roll relative to the soil as the implement 10 is moved across the field such that the fingers 50 break up and/or sweep away residue and dirt clods. Additionally, the residue removal device 46 may include a support arm 52 configured to adjustably couple the residue removal wheel(s) 48 to the frame assembly 24. For example, one end of the support arm 52 may be pivotally coupled to the wheel(s) 48, while an opposed end of the support arm 52 may be pivotally coupled to the frame 24. However, it should be appreciated that, in alternative embodiments, the residue removal wheel(s) 48 may be coupled to the frame 24 in any other suitable manner. Furthermore, although only one residue removal wheel 48 is shown in FIG. 2, it should be appreciated that, in alternative embodiments, the residue removal device 46 may include any other suitable number of residue removal wheels 48. For example, in one embodiment, the residue removal device 46 may include a pair of residue removal wheels 48.

In several embodiments, an actuator 110 may be configured to move or otherwise adjust the position of the residue removal device 46 relative to the frame 24. For example, as shown in the illustrated embodiment, a first end of the actuator 110 (e.g., a rod 112 of the actuator 110) may be coupled to the support arm 52 of the residue removal device 46, while a second end of the actuator 110 (e.g., the cylinder 114 of the actuator 110) may be coupled to a bracket 54, which is, in turn, coupled to the frame 24. The rod 112 of the actuator 110 may be configured to extend and/or retract relative to the cylinder 114 to adjust the downforce being applied to the residue removal wheel(s) 48. As such, increasing the downforce being applied to the residue removal wheel(s) 48 may increase the aggressiveness with which the removal wheels) 48 breaks up and sweeps away the residue and/or dirt clods. Conversely, decreasing the downforce being applied to the residue removal wheel(s) 48 may decrease the aggressiveness with which the removal wheel (s) 48 breaks up and sweeps away the residue and/or dirt clods. In the illustrated embodiment, the actuator 110 corresponds to a fluid-driven actuator, such as hydraulic or pneumatic cylinder. However, it should be appreciated that the actuator 110 may correspond to any other suitable type of actuator, such as an electric linear actuator.

Furthermore, in one embodiment, one or more rotational speed sensors 116 may be provided in operative association with one or more of the ground engaging assemblies of the row unit 18. For example, a rotational speed sensor 116 may be associated with the closing discs 38 of the furrow closing assembly 36, the opening discs 34 of the opening assembly 28, and the residue removal device 46. As such, each the rotational speed sensor 116 may be configured to detect a parameter associated with the rotational speed of the respective rotating ground engaging tools 34, 38, 46 as the implement 10 is moved across the field. For example, in one embodiment, one or more of the rotational speed sensors 116 may be configured as a Hall Effect sensor configured to detect the rotational speed of the ground engaging tools, e.g., the closing disc(s) 38, relative to an axle or shaft on which the closing disc(s) 38 are mounted relative to the support arm 40. However, it should be appreciated that, in alternative embodiments, the rotational speed sensor 116 may be configured as any other suitable device for sensing or detecting the rotational speed of the closing disc(s) 38. As will be described below, in some embodiments, the rotational speed of the closing disc(s) 38 may be indicative of "plugging" of the furrow closing assembly 36. In general, the closing discs 38 may not rotate freely relative to the ground when the furrow closing assembly 36 is plugged.

Moreover, in one embodiment, one or more plugging sensors 120 may be provided in operative association with one or more of the ground engaging assemblies of the row unit 18. For example, a plugging sensor 120 may be associated with the closing discs 38 of the furrow closing assembly 36, the opening discs 34 of the opening assembly 28, and the residue removal device 46. Specifically, in several embodiments, the plugging sensor 120 may be configured to capture data indicative of plugging of the associated ground engaging assembly, e.g. the furrow closing assembly 36. In general, the furrow closing assembly 36 may be plugged when soil and/or residue become trapped between, in front of, and/or behind adjacent closing discs 38 in a manner that prevents the soil from flowing through the furrow closing assembly 36 as the implement 10 is moved across the field. In one embodiment, the plugging sensor 120 may be a vision-based or Radio Detection and Ranging (RADAR) based sensor mounted or installed on the row unit 18 such that the plugging sensor 120 has a field of view or sensor detection range (e.g., as indicated by dashed lines 122 in FIG. 2) directed towards the closing discs 38 of the furrow closing assembly 36. As such, the plugging sensor 120 may be configured to capture plugging data (e.g., vision-based or Radio Detection and Ranging (RADAR) based data) of the soil flowing through the furrow closing assembly 36 as the implement 10 is moved across the field.

Additionally, in one embodiment, one or more residue sensors 124 may be provided in operative association with the row unit 18. Specifically, in several embodiments, the residue sensor 124 may be configured to capture data indicative of the presence and/or amount of residue within at least a portion of the field across which the implement 10 is being moved. For example, in one embodiment, the residue sensor 124 may be a vision-based or Radio Detection and Ranging (RADAR) based sensor mounted or installed on the support arm 52 of the residue removal device 46 such that the residue sensor 124 has a field of view or sensor detection range (e.g., as indicated by dashed lines 126 in FIG. 2) directed towards the furrow being formed by the furrow opening assembly 28. As such, the residue sensor 124 may be configured to capture residue data (e.g., vision-based or RADAR-based data) of the furrow being formed as the implement 10 is moved across the field, with such residue data being indicative of the presence of residue within the furrow. It should be appreciated that, in alternative embodiments, the residue sensor 124 may be installed at any other suitable location(s) on the row unit 18 or the implement 10. For example, in one embodiment, the residue sensor 124 may be mounted on the row unit 18 (e.g., on the frame 24) such that the sensor 124 is configured to capture data of a section of the field in front of the row unit 18. Additionally, it should be appreciated that the implement 10 may only include one residue sensor 124 (e.g., mounted on the toolbar 12) or one or more residue sensors 124 mounted on each of the row units 18.

Moreover, it should be appreciated that the plugging sensor 120 and/or the residue sensor 124 may correspond to any suitable sensing device(s) configured to detect or capture vision-based data (e.g., images, point cloud data, and/or the like) or RADAR-based data associated with the soil and/or residue present within an associated field of view. For example, in several embodiments, the plugging sensor 120 and/or the residue sensor 124 may correspond to Light Detection and Ranging (LIDAR) sensors or RADAR sensors. However, in alternative embodiments, the plugging sensor 120 and/or the residue sensor 124 may correspond to any other suitable vision-based or beam-based sensing device(s), such as optical beam sensors and/or cameras.

It should be appreciated that the configuration of the row unit 18 described above and shown in FIG. 2 is provided only to place the present subject matter in an exemplary field of use. Thus, it should be appreciated that the present subject matter may be readily adaptable to any manner of row unit configuration or ground engaging assembly of such row unit, e.g., the furrow opening assembly 28.

Figure 3:
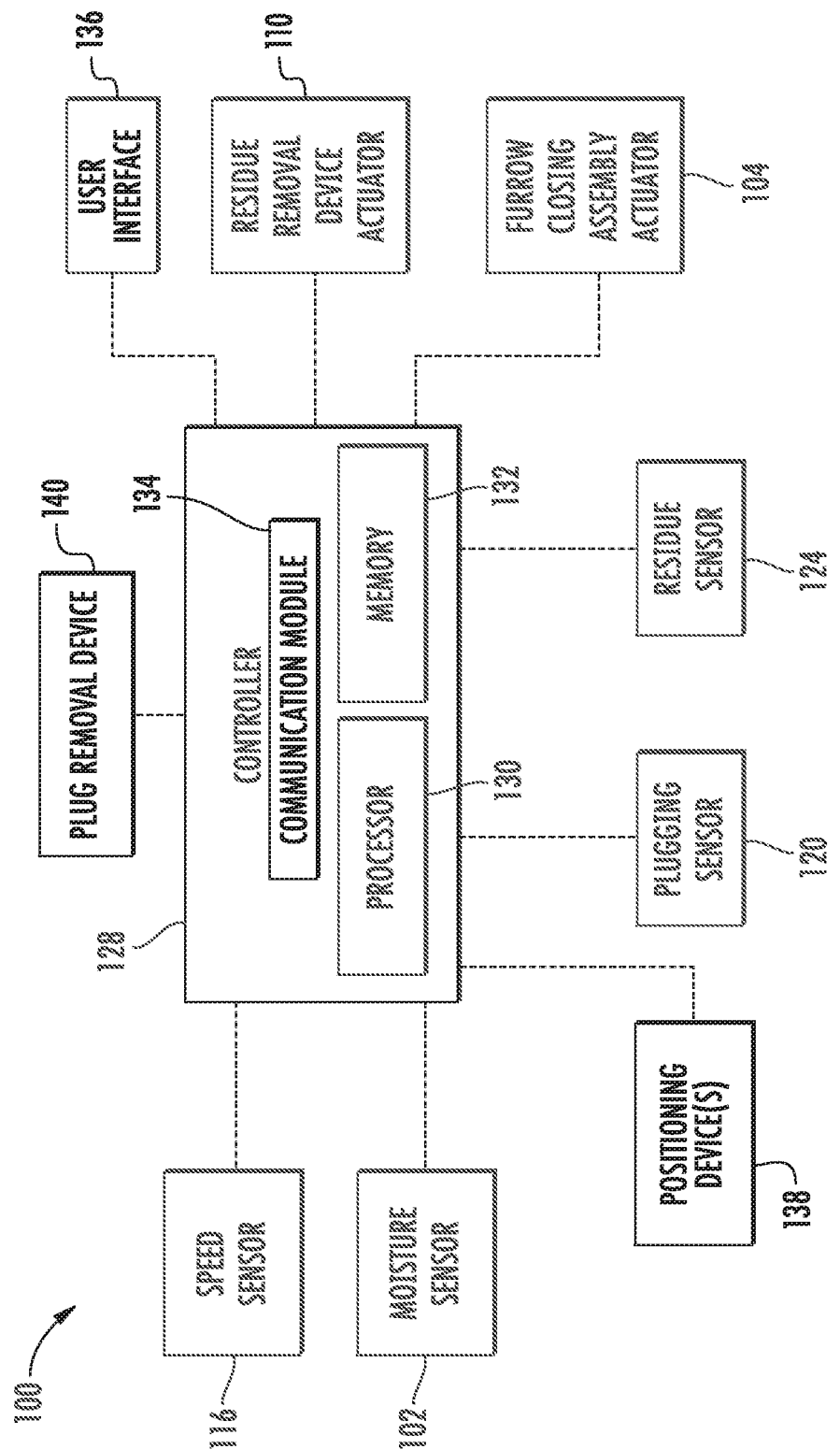
FIG. 3 illustrates a schematic view of one embodiment of a system for managing material accumulation relative to a ground engaging assembly of an agricultural implement in accordance with aspects of the present subject matter.

Referring now to FIG. 3, a perspective view of one embodiment of a system 100 for managing material accumulation relative to a ground engaging assembly of an agricultural implement is illustrated in accordance with aspects of the present subject matter. In general, the system 100 will be described herein with reference to the implement 10 and row unit 18 described above with reference to FIGS. 1 and 2. However, it should be appreciated by those of ordinary skill in the art that the disclosed system 100 may generally be utilized with seed-planting implements having any other suitable implement configuration and/or row units having any other suitable row unit configuration.

As shown in FIG. 3, the system 100 may include a controller 128 and various other components configured to be communicatively coupled to and/or controlled by the controller 128, such as a furrow closing assembly actuator 104, a residue removal device actuator 110, and/or various sensors configured to monitor one or more parameters associated with material accumulation relative to one or more ground engaging tools of a row unit (e.g., moisture sensors 102, rotational speed sensors 116, plugging sensors 120, and/or residue sensors 124). As will be described below, the controller 128 may be configured to execute one or more routines for managing material accumulation relative to ground engaging assemblies of an implement 10, e.g., the closing disc(s) 38 of a closing assembly 36 of the implement 10, based on data received from at least one of the sensors configured to provide an indication of the plugging or accumulation type of the material accumulation. For instance, in one embodiment, when it is determined that the closing discs 38 are plugged, the disclosed control routine may be used to more effectively and efficiently manage material accumulation relative ground engaging tools by choosing an appropriate control action based on the accumulation type.

For purpose of description, the control routine will generally be described herein as being used to manage material accumulation relative to closing discs 38 of the planting implement 10. However, it should be appreciated that such routine may also be used to manage material accumulation relative to any other suitable ground engaging tool of any other suitable implement type, such as the opening discs 34 and/or the residue removal device 46 of a row unit 18 and/or discs and/or rolling baskets of a tillage implement.

In general, the controller 128 may comprise any suitable processor-based device known in the art, such as a computing device or any suitable combination of computing devices. Thus, in several embodiments, the controller 128 may include one or more processor(s) 130 and associated memory device(s) 132 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 132 of the controller 128 may generally comprise memory element(s) including, but not limited to, a computer readable medium (e.g., a random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 132 may generally be configured to store suitable computer-readable instructions that, when implemented by the processor(s) 130, configure the controller 128 to perform various computer-implemented functions, such as one or more aspects of the management control algorithm or routine 200 described below with reference to FIG. 4 and one or more aspects of the method 300 described below with reference to FIG. 5. In addition, the controller 128 may also include various other suitable components, such as one or more input/output channels, a data/control bus and/or the like.

It should be appreciated that the controller 128 may correspond to an existing controller of the implement 10 or an associated work vehicle (not shown) or the controller 128 may correspond to a separate processing device. For instance, in one embodiment, the controller 128 may form all or part of a separate plug-in module that may be installed within the implement 10 or associated work vehicle to allow for the disclosed system and method to be implemented without requiring additional software to be uploaded onto existing control devices of the implement 10 or the associated work vehicle.

In some embodiments, the controller 128 may include a communications module or interface 134 to allow for the controller 128 to communicate with any of the various other system components described herein. For instance, one or more communicative links or interfaces (e.g., one or more data buses), may be provided between the communications interface 134 and the various sensors 102, 116, 120, 124 to allow the controller 128 to receive data inputs from the one or more sensors. In this regard, the controller 128 may be configured to process or analyze the received data from the various sensors 102, 116, 120, 124 to identify associated field conditions or operating parameters of the closing assembly 36. For instance, the controller 128 may include a lookup-up table, suitable mathematical formula, data processing techniques, and/or algorithms stored within its memory 132 that correlate the received data from the sensors(s) to associated field conditions or operating parameters. Additionally, one or more communicative links or interfaces (e.g., one or more data buses), may be provided between the communications interface 134 and the components controlled by the controller 128 (e.g., actuators 104, 110) to allow the controller 128 to send control signals for controlling the operation of such components. It should be appreciated that the controller 128 may be communicatively coupled to the sensor(s) 102, 116, 120, 124 and the components 104, 110 via any suitable connection, such as a wired or wireless connection.

Furthermore, in some embodiments, the system 100 may also include a user interface 136 in communication with the controller 128. More specifically, the user interface 136 may be configured to provide feedback (e.g., notifications associated with the operational parameters of the furrow closing assembly 36) to the operator of the implement 10. As such, the user interface 136 may include one or more feedback devices (not shown), such as display screens, speakers, warning lights, and/or the like, which are configured to communicate such feedback. In addition, some embodiments of the user interface 136 may include one or more input devices (not shown), such as touchscreens, keypads, touchpads, knobs, buttons, sliders, switches, mice, microphones, and/or the like, which are configured to receive user inputs from the operator. In one embodiment, the user interface 136 may be positioned within a cab of a work vehicle configured to tow the implement 10 across the field. However, in alternative embodiments, the user interface 136 may have any suitable configuration and/or be positioned in any other suitable location.

Further still, the controller 128 may be communicatively coupled to one or more positioning devices 138 installed relative to the implement 10. In one embodiment, the positioning device(s) 138 may be configured to determine the exact location of the implement 10 using a satellite navigation position system (e.g. a GPS system, a Galileo positioning system, the Global Navigation satellite system (GLONASS), the BeiDou Satellite Navigation and Positioning system, and/or the like). In such an embodiment, the location determined by the positioning device(s) 138 may be stored (e.g., in the form coordinates) for subsequent processing and/or analysis. For instance, based on the known dimensional configuration and/or relative positioning between the implement 10 and a marker assembly, the determined location from the positioning device(s) 138 may be used to geo-locate each sensor 102 and/or its associated data within the field.

By continuously monitoring the location of the implement 10 as passes are made across the field and by processing the sensor data to estimate or determine one or more parameters associated with the field condition(s), one or more maps may be generated over time that correlate field condition data to various locations along the field. For instance, in one embodiment, the location coordinates derived from the positioning device(s) 138 and the sensor data received from the sensor(s) may both be time-stamped. In such an embodiment, the time-stamped data may allow the sensor data generated by the sensor(s) to be matched or correlated to a corresponding set of location coordinates received or derived from the positioning device(s) 138. As such, based on the data collected using the residue sensor 124 and/or the moisture sensor 102, a crop residue map may be generated that geo-locates the monitored crop residue data within the field and/or a moisture content map may be generated that geo-locates the monitored soil moisture data within the field. Alternatively, field maps, such as crop residue maps and/or moisture content maps, may be generated based on data collected during previous field operations, such as historical data collected at any point in time prior to the performance of the current agricultural operation.

It should be appreciated that, as used herein, a "map" may generally correspond to any suitable dataset that correlates data to various locations within a field. Thus, for example, a map may simply correspond to a data table that correlates field condition data to various locations along the swath being mapped or may correspond to a more complex data structure, such as a geospatial numerical model that can be used to identify detected variations in the field condition data and classify such variations into geographic zones or groups, which may, for instance, then be used to generate a graphically displayed map or visual indicator. Further, while the crop residue map and the moisture content map are described separately, the crop residue and moisture content data may be part of the same map correlating both field conditions to a given position in the field.

Figure 4:
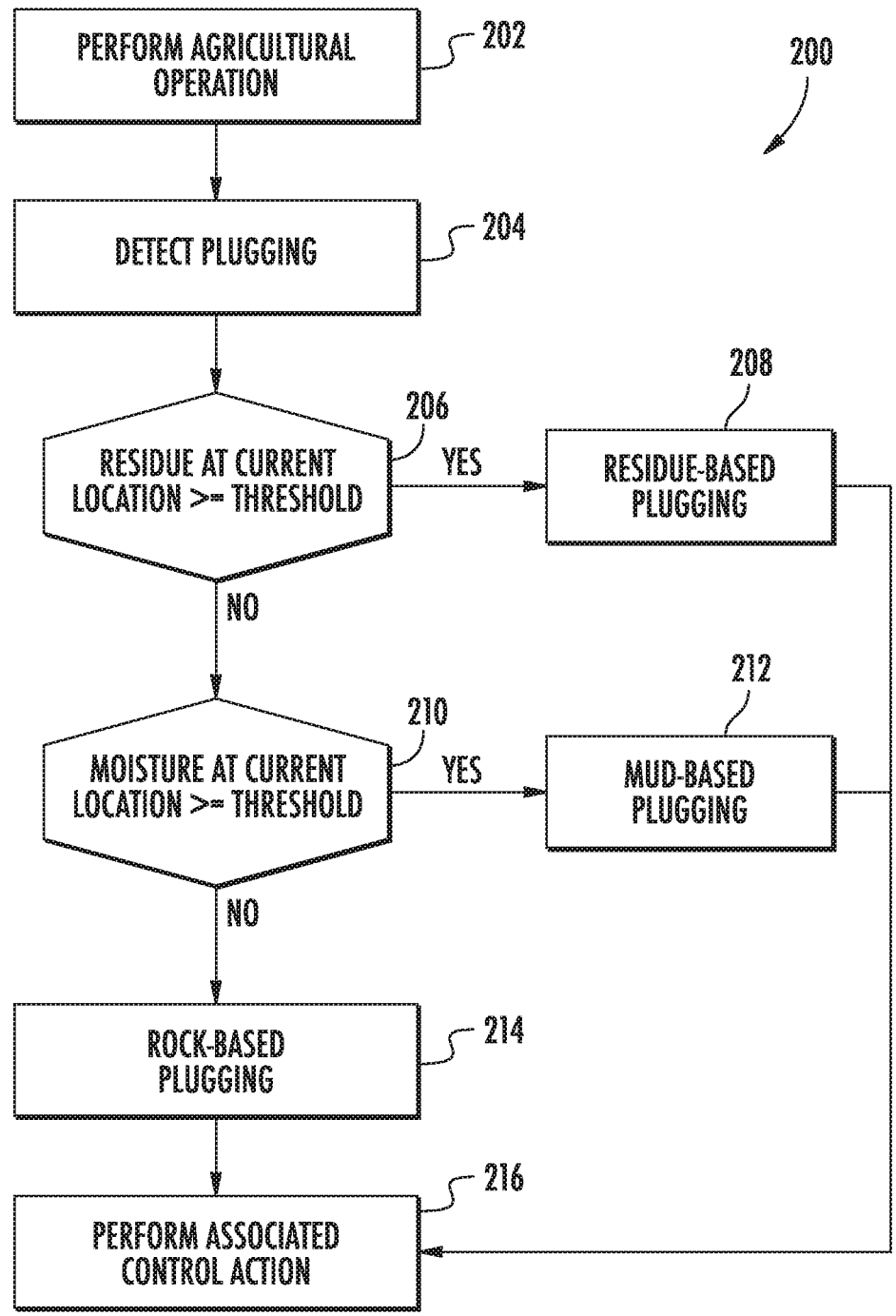
FIG. 4 illustrates a flow diagram of one embodiment of a control algorithm for managing material accumulation relative to a ground engaging assembly of an agricultural implement in accordance with aspects of the present subject matter.

Referring now to FIG. 4, a flow diagram of one embodiment of a control algorithm 200 that may be executed when managing material accumulation relative to a ground engaging assembly of an agricultural implement is illustrated in accordance with aspects of the present subject matter. In general, the control algorithm 200 will be described herein as being implemented by the controller 128 of the system 100 described above with reference to FIG. 3. However, it should be appreciated that the various processes described below may alternatively be implemented by another computing device or any combination of computing devices. In addition, although FIG. 4 depicts control steps or functions performed in a particular order for purposes of illustration, the management routines discussed herein are not limited to any particular order or arrangement. One skilled in the art, using the disclosures provided herein, will appreciate that the various steps or functions of the algorithms disclosed herein can be omitted, rearranged, combined, and/or adapted in various ways without deviating from the scope of the present disclosure.

As shown in FIG. 4, during performance of an agricultural operation, such as a planting operation, at (202), a plug or excessive material accumulation relative to ground engaging tools, such as closing discs 38, may be detected at (204) based on the data received from one or more of the sensors configured to detect material accumulation, such as the speed sensor(s) 116 and/or plugging sensor(s) 120 communicatively coupled to the controller 128. As described above with reference to FIG. 3, the controller 128 may include one or more suitable algorithms stored within its memory 132 that, when executed by the processor 130, allow the controller 128 to determine the presence and/or amount of material accumulation relative to the corresponding around engaging tool(s) based on the data received from the sensors 116, 120.

For example, when the closing disc(s) 38 are plugged with soil and/or residue, the closing disc(s) 38 may be unable to rotate freely as the implement 10 is moved across the field such that the rotational speed of the closing disc(s) 38 is reduced. As such, the controller 128 may be configured to compare the values associated with the rotational speed of the closing disc(s) 38 to a minimum rotational speed threshold. Thereafter, in the event that the values of the monitored rotational speed falls below the minimum rotational speed threshold (thereby indicating that the closing disc(s) 38 are not rotating freely), the controller 128 may be configured to determine that the furrow closing assembly 36 is plugged.

Alternatively or additionally, the data received from the plugging sensor 120 may be indicative of the soil flowing through the furrow closing assembly 36 as the implement 10 is moved across the field. In this regard, the controller 128 may be configured, as described above, to process or analyze the received data to determine when the furrow closing assembly 36 is plugged or soil is otherwise not properly flowing through the furrow closing assembly 36 to determine when the furrow closing assembly 36 is plugged.

The controller 128 may be configured to monitor the status of the material accumulation relative to the corresponding ground engaging tool(s) periodically, continuously, or only as demanded by an operator of the implement 10. For example, in some embodiments, the controller 128 may collect data from one or more of the sensor(s) 116, 120 periodically based on some predetermined delay period or sampling frequency, such as after a predetermined period of time (e.g., a set amount of operating time), after a certain operating distance covered (e.g., a set amount of acres worked by the implement 10), and/or the like.

After a plug is detected, the controller 128 may be configured to estimate or identify the "accumulation type" of the material accumulated relative to the tool(s). For example, as shown in FIG. 4, at (206), the controller may be configured to assess the likelihood that the plugging is caused primarily by crop residue. More particularly, the controller 128 may be configured to determine whether the amount of residue within the field (e.g., at or adjacent to the implement's current location in the field, including field locations over which the implement has been previously passed) is greater than or equal to a predetermined crop residue threshold. Specifically, in one embodiment, the controller 128 may be configured to access a crop residue map, as described above, that comprises historical crop residue data associated with the field. In such instance, the controller 128 may be configured to retrieve the amount of residue corresponding to the implement's current location and/or previous locations over which the implement has passed (e.g., as determined by the positioning device(s) 138) from the stored crop residue map. In another embodiment, the controller 128 may access or receive data corresponding to the amount of residue at or adjacent to the current location of the implement 10 from the residue sensor 124, such as by accessing such data as it is being generated by the sensor 124. It should be appreciated that, in some embodiments, the predetermined crop residue threshold may be, for example, an input provided by the operator via the user interface 136. However, in other embodiments, the predetermined crop residue threshold may be found or selected in any other suitable way, such as from a look-up table stored in the controller 128, for example.

In the event that the amount of residue at or adjacent to the current location of the implement 10 is greater or equal to the predetermined crop residue threshold, the controller 128 may, at (208), be configured to estimate that the plugging or accumulation type is primarily residue-based. Thereafter, an associated control action may be performed at (216), as will be described in greater detail below. It should be appreciated that, as used herein, a "residue-based" accumulation type generally refers to material accumulation that is mainly comprised of, or more than half of the material accumulation is comprised of, residue, and that the remainder of the material accumulation may be comprised of any other field material, such as rock, debris, or soil.

In the event that the amount of residue at or adjacent to the current location of the implement 10 is less than the predetermined crop residue threshold at (206), the controller 128 may be configured to determine whether the plugging is, instead, caused primarily by another field material, such as rocks or mud. More specifically, the controller 128 may be configured to determine whether the plugging is caused by rocks or mud by comparing, at (210) the moisture content at or adjacent to the current location of the implement 10 (including previous locations over which the implement has passed) to a predetermined soil moisture threshold. Similar to the crop residue data, moisture content data may be accessed by the controller 128 by accessing a moisture content map, as described above, that comprises historical soil moisture data associated with the soil within the field at or adjacent to the current location of the implement 10. In such instance, the controller 128 may be configured to retrieve the moisture content corresponding to the implement's current location and/or previous locations over which the implement has passed (e.g., as determined by the positioning device(s) 138) from the stored moisture content map. In another embodiment, the controller 128 may access or receive data corresponding to the moisture content of the soil within the field at or adjacent to the current location of the implement 10 via the moisture sensor 102, such as by accessing such data as it is being generated by the sensor 102. It should be appreciated that, similar to the predetermined crop residue threshold, the predetermined soil moisture threshold may be input by a user at a user interface 136 or may be selected, e.g., from a look-up table stored in the controller 128.

In the event that the moisture content of the soil at the current location of the implement 10 is greater than or equal to the soil moisture threshold (e.g., at (210)), the controller 128 may determine that the soil is wet and likely "muddy" and, thus, may estimate, at (212), that the accumulation type is primarily mud-based. Thereafter, an associated control action may be performed at (216), as will be described below. It should be appreciated that, as used herein, a "mud-based" accumulation type generally refers to material accumulation that is mainly comprised of, or more than half of the material accumulation is comprised of, muddy soil, and that the remainder of the material accumulation may be comprised of any other field material, such as rock, debris, or residue.

In the event that the moisture content of the soil at or adjacent to the current location of the implement 10 is less than the predetermined moisture threshold at (210), the controller 128 may determine that the soil is relatively dry and, thus, may estimate, at (214), that the accumulation type is primarily rock-based or debris-based. Thereafter, an associated control action may be performed at (216), as will be described below. It should be appreciated that, as used herein, a "rock-based" accumulation type generally refers to material accumulation that is mainly comprised of, or more than half of the material accumulation is comprised of, rocks or non-residue/non-soil debris, and that the remainder of the material accumulation may be comprised of any other field material, such as soil or residue.

It should be appreciated that, in some embodiments, it may be desirable to further confirm the accumulation type of the material accumulation. For instance, after determining residue-based plugging at (208), the moisture content of the soil at or adjacent to the current location of the implement 10 (including previous locations over which the implement has passed) may be compared to a further predetermined soil moisture threshold. The further predetermined soil moisture threshold is generally greater than the predetermined soil moisture threshold at (210). In the event that the moisture content at or adjacent to the current location of the implement 10 is greater than the further predetermined soil moisture threshold, the controller 128 may determine that the soil is wet and likely "muddy" and, thus, may instead estimate that the accumulation type is primarily mud-based. Alternatively, in the event that the moisture content of the soil at or adjacent to the current location of the implement 10 is less than the further predetermined moisture threshold, the controller 128 may determine that the soil is relatively dry and, thus, may confirm the estimate that the accumulation type is residue-based.

As will be described in greater detail in the below, certain control actions that may be useful in managing material accumulation when the accumulation type is, e.g., residue-based, may not be useful in managing material accumulation when the accumulation type is, e.g., mud-based. As such, the controller 128 may determine an appropriate control action to most effectively manage the material accumulation based on the accumulation type. It should be appreciated that the specific control action(s) to be performed based on the determined accumulation type may be tool-specific. For instance, examples of suitable control actions for de-plugging a closing assembly 36 of a row unit will generally be described below. A different control strategy may be necessary, for example, to de-plug a different tool (e.g., a rolling basket of a tillage implement) based on the determined accumulation type.

In some embodiments, the controller 128 may transmit control signals to the actuator 104 of the furrow closing assembly 36 instructing the actuator 104 to move the furrow closing assembly 36 from its operating or working position, where the closing disc(s) 38 are positioned to work the soil, to a raised position, wherein the closing disc(s) 38 are raised out of the soil, and subsequently back to the operating position. Such movement of the furrow closing assembly 36 may help facilitate de-plugging when rock-based or residue-based accumulation exists to at least partially remove the rocks/debris and/or residue trapped relative to the furrow closing assembly 36. Alternatively, the controller 128 may be configured to transmit control signals to the actuator 104 instructing the actuator 104 to adjust (i.e., increase) the downforce applied to the furrow closing assembly 36. By changing the downforce applied to the furrow closing assembly 36, material accumulation, particularly rock or residue, trapped relative to the furrow closing assembly 36 may be released.

It should be appreciated that, in other embodiments, components of the furrow closing assembly 36 may be actuated in a different manner to perform a control action in response to a respective accumulation type. For example, in one embodiment, the closing discs 38 of each row unit 18 may be selectively actuatable relative to each other to change (e.g., increase or decrease) a lateral distance and/or a vertical distance from each other. In such instance, the controller 128 may be configured to transmit control signals to actuate one or more of the discs 38 relative to the other of discs 38 upon detection of a plugged condition, and subsequently back to the working position. Such movement of the closing discs 36 of the furrow closing assembly 36 may at least partially remove rocks/debris or residue trapped relative to the furrow closing assembly 36, in addition to potentially reducing the amount of mud trapped relative to the furrow closing assembly 36.

In some embodiments, the controller 128 may transmit control signals to the actuator 110 associated with the residue removal device 46 to perform a control action. For example, in instances in which the plugging is most likely residue-based, the controller 128 may increase the downforce being applied to the residue removal device 46 in a manner that causes the residue removal device 46 to more aggressively break up and sweep residue out of the path of the implement 10, such that less residue accumulates relative to the closing assembly 36. Conversely, in instances in which the plugging is most likely mud-based, the controller 128 may not adjust the downforce of the residue removal device 46, as increased aggressiveness in breaking up and removing residue and dirt clods from the path of the implement 10 may be unlikely to prevent further plugging.

Further, in some embodiments, the controller 128 may be configured to transmit control signals to slow down or stop the implement 10, e.g., at the end of a row in the field, so that the operator may manually manage, e.g. reduce, the material accumulated. Such slowing down or stopping of the implement 10 may particularly be useful when the accumulation type is mud-based.

In some embodiments, the controller 128 may further be configured to transmit control signals to one or more plug removal devices 140 (FIG. 3) provided in operative association with one or more of the ground engaging assemblies of the row unit 18. Each plug removal device 140 may be configured as an actuatable tool that, when actuated by the controller 128, works to manage, e.g., reduce, the material accumulated. Such plug removal device 128 may be particularly useful when the accumulation type is mud-based.

Additionally or alternatively, in one embodiment, the controller 128 may be configured to notify the operator of the implement 10 that the furrow closing assembly 36 is plugged and further indicate the accumulation type of the material accumulation. Specifically, the controller 128 may provide a notification to the operator of the implement 10 via the user interface 136 (e.g., by causing a visual or audible notification or indicator to be presented to the operator) that provides an indication that the furrow closing assembly 36 is plugged and further indicate the accumulation type of the material accumulation. In such instances, the operator may then choose to initiate any suitable control action he/she believes is necessary, e.g., adjusting the downforce applied to the residue removal device 46, adjusting the position of the furrow closing assembly 36, operating the plug removal device(s) 140, and/or stopping the implement 10, to effectively manage the material accumulation. For instance, the operator may choose to stop the implement 10 when the accumulation type is mud-based to manually remove the material accumulation. Additionally or alternatively, the controller 128 may suggest suitable control actions, as provided above, based on the accumulation type of the material accumulation.

Figure 5:
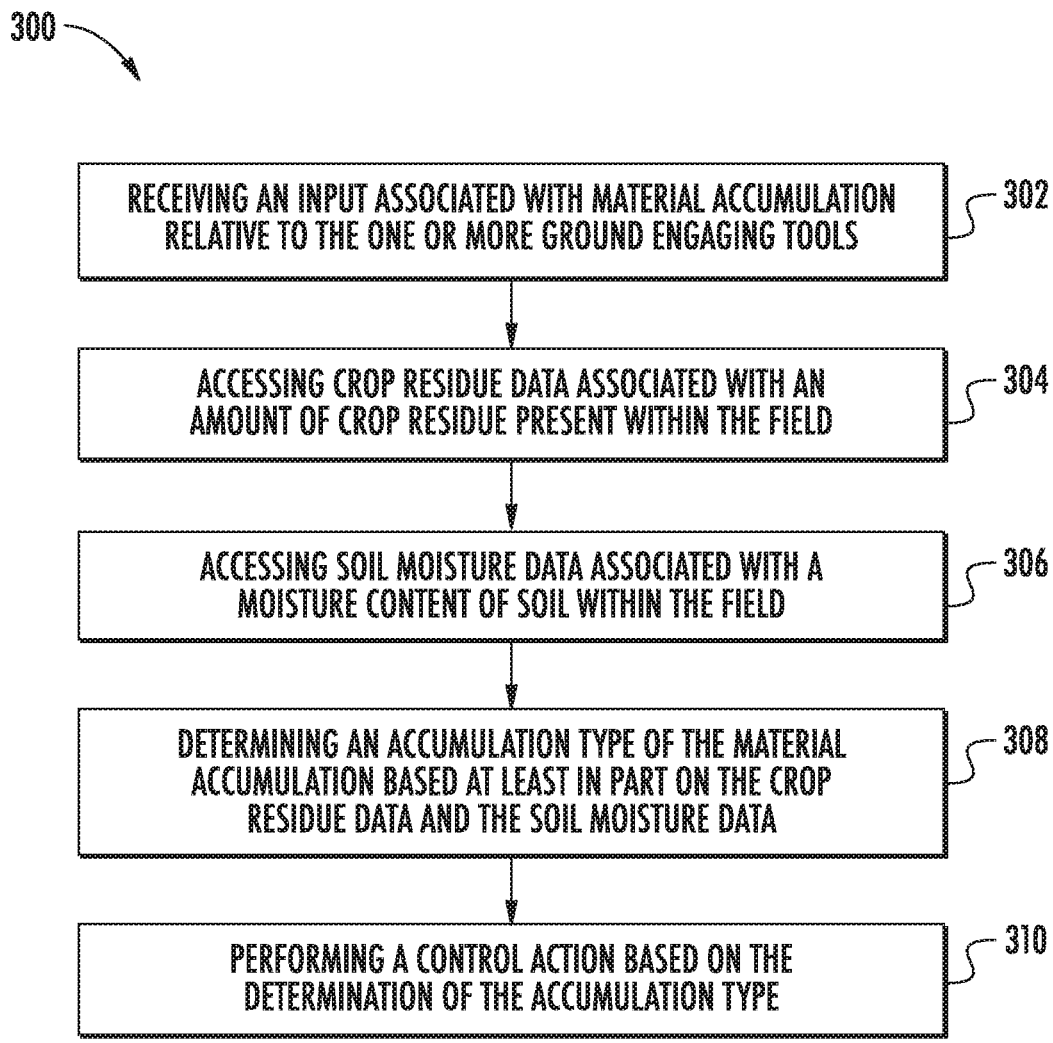
FIG. 5 illustrates a flow diagram of one embodiment of a method for managing material accumulation relative to a ground engaging assembly of an agricultural implement in accordance with aspects of the present subject matter.

Referring now to FIG. 5, a flow diagram of one embodiment of a method 300 for managing material accumulation relative to a ground engaging assembly of an agricultural implement is illustrated in accordance with aspects of the present subject matter. In general, the method 300 will be described herein with reference to the system 100 described above with reference to FIG. 3. However, it should be appreciated by those of ordinary skill in the art that the disclosed method 300 may be implemented within any other system. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (302), the method 300 may include receiving an input associated with material accumulation relative to the one or more ground engaging tools. For instance, as described above, a rotational speed sensor 116 may detect that a rotational speed of one or more ground engaging tools has fallen below a minimum rotational speed threshold, which indicates that the tool(s) is plugged. Alternatively or additionally, as described above, a plugging sensor 120 may detect that soil is no longer flowing relative to the ground engaging tool(s), which indicates that the tool(s) is plugged.

Further, at (304), the method 300 may include accessing crop residue data associated with an amount of crop residue present within the field. For instance, as described above, crop residue data, such as a presence and/or amount of crop residue at or adjacent to the current location of the implement 10, may be accessed and retrieved from a crop residue map comprising historical crop residue data associated with the current position in the field. Alternatively or additionally, as described above, the presence and/or amount of crop residue may be actively measured with the residue sensor 124.

Additionally, at (306), the method 300 may include accessing soil moisture data associated with a moisture content of soil within the field. For instance, as described above, soil moisture data, such as a moisture content of soil within the field at or adjacent to the current location of the implement 10, may be accessed and retrieved from a moisture content map comprising historical soil moisture data associated with the current position in the field. Alternatively or additionally, as described above, the moisture content of the soil may be actively measured with the moisture sensor 102.

Furthermore, at (308), the method 300 may include determining an accumulation type of the material accumulation based at least in part on the crop residue data and the soil moisture data. For instance, as described above, the accumulation type of the material accumulation relative to the ground-engaging tools may be determined by comparing the crop residue data and the soil moisture data to one or more relevant thresholds to identify the likelihood that the accumulation is mainly residue-based, mud-based, or rock-based.

Moreover, at (310), the method 300 may include performing a control action based on the determination of the accumulation type of the material accumulation relative to the ground engaging tool(s). For instance, as described above, the control action may include automatically controlling one or more components of the implement 10 (e.g., by controlling the furrow closing assembly actuator 104 and/or the residue removal device actuator 110), slowing down or stopping the implement 10, and/or notifying the operator, with the control action generally being selected based on the determined accumulation type.

It is to be understood that, in several embodiments, the steps of the routine 200 and method 300 are performed by the controller 128 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, in several embodiments, any of the functionality performed by the controller 128 described herein, such as the routine 200 and method 300, are implemented in software code or instructions which are tangibly stored on a tangible computer readable medium. The controller 128 loads the software code or instructions via a direct interface with the computer readable medium or via a wired and/or wireless network. Upon loading and executing such software code or instructions by the controller 128, the controller 128 may perform any of the functionality of the controller 128 described herein, including any steps of the routine 200 and method 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code. Which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for managing material accumulation during operation of an agricultural implement, comprising:
   a ground engaging assembly including one or more ground engaging tools configured to engage soil within a field as the agricultural implement is moved across the field;
   a sensor detecting material accumulation relative to the one or more ground engaging tools; and
   a controller communicatively coupled to the sensor, the controller including a processor and an associated memory, the memory including instructions that, when implemented by the processor, configure the controller to:
      receive an input from the sensor associated with material accumulation relative to the one or more ground engaging tools;
      access crop residue data associated with an amount of crop residue present within the field;
      access soil moisture data associated with a moisture content of soil within the field; and
      determine an accumulation type of the material accumulation based at least in part on the crop residue data and the soil moisture data.

2. The system of claim 1, further comprising a residue sensor in communication with the controller, the residue sensor configured to provide an indication of the amount of crop residue within the field as the agricultural implement is moved across the field.

3. The system of claim 1, further comprising a moisture sensor in communication with the controller, the moisture sensor configured to provide an indication of the moisture content of the soil within the field as the agricultural implement is moved across the field.

4. The system of claim 1, wherein the crop residue data comprises historical crop residue data associated with the field.

5. The system of claim 1, wherein the soil moisture data comprises historical soil moisture data associated with the soil within the field.

6. The system of claim 1, wherein the controller is configured to:
   compare the amount of crop residue present within the field to a predetermined residue threshold; and
   compare the moisture content of the soil within the field to a predetermined moisture threshold.

7. The system of claim 6, wherein the controller is further configured to identify the accumulation type as mud-based accumulation when the amount of crop residue present within the field is less than the predetermined residue threshold and the moisture content of the soil within the field is greater than the predetermined moisture threshold.

8. The system of claim 6, wherein the controller is further configured to identify the accumulation type as rock-based accumulation when the amount of crop residue present within the field is less than the predetermined residue threshold and the moisture content of the soil within the field is less than the predetermined moisture threshold.

9. The system of claim 6, wherein the controller is further configured to identify the accumulation type as residue-based accumulation when the amount of crop residue present within the field is greater than the predetermined residue threshold.

10. The system of claim 1, wherein the controller is further configured to perform a control action based on the determination of the accumulation type of the material accumulation relative to the one or more ground engaging tools.

11. A method for managing material accumulation relative to a ground engaging assembly of an agricultural implement, the ground engaging assembly including one or more ground engaging tools configured to engage soil within a field as the agricultural implement is moved across the field, the method comprising:
   receiving, with a computing device, an input associated with material accumulation relative to the one or more ground engaging tools;
   accessing, with the computing device, crop residue data associated with an amount of crop residue present within the field;
   accessing, with the computing device, soil moisture data associated with a moisture content of soil within the field;
   determining, with the computing device, an accumulation type of the material accumulation based at least in part on the crop residue data and the soil moisture data; and
   performing, with the computing device, a control action based on the determination of the accumulation type of the material accumulation relative to the one or more ground engaging tools.

12. The method of claim 11, further comprising:
   comparing, with the computing device, the amount of crop residue present within the field to a predetermined residue threshold; and
   comparing, with the computing device, the moisture content of the soil within the field to a predetermined moisture threshold.

13. The method of claim 12, further comprising identifying, with the computing device, the accumulation type as mud-based accumulation when the amount of crop residue present within the field is less than the predetermined residue threshold and the moisture content of the soil within the field is greater than the predetermined moisture threshold.

14. The method of claim 12, further comprising identifying, with the computing device, the accumulation type as rock-based accumulation when the amount of crop residue present within the field is less than the predetermined residue threshold and the moisture content of the soil within the field is less than the predetermined moisture threshold.

15. The method of claim 12, further comprising identifying, with the computing device, the accumulation type as residue-based accumulation when the amount of crop residue present within the field is greater than the predetermined residue threshold.

16. The method of claim 11, wherein accessing the crop residue data comprises accessing sensor data received from a residue sensor configured to provide an indication of the amount of crop residue within the field as the agricultural implement is moved across the field.

17. The method of claim 11, wherein accessing the soil moisture data comprises accessing sensor data received from a moisture sensor configured to provide an indication of the moisture content of the soil within the field as the agricultural implement is moved across the field.

18. The method of claim 11, wherein accessing the crop residue data comprises accessing a crop residue map comprising historical crop residue data associated with the field.

19. The method of claim 11, wherein accessing the soil moisture data comprises accessing a moisture content map comprising historical soil moisture data associated with the soil within the field.

20. The method of claim 11, wherein performing the control action comprises at least one of notifying an operator of the agricultural implement of the accumulation type, adjusting a position of the ground engaging assembly between an operating position relative to the ground and a raised position relative to the ground, adjusting a downforce being applied to the ground engaging assembly, or stopping the agricultural implement.

* * * * *